United States Patent [19]

Osterholm

[11] Patent Number: 4,795,423
[45] Date of Patent: Jan. 3, 1989

[54] OXYGENATED PERFLUORINATED PERFUSION OF THE OCULAR GLOBE TO TREAT ISCHEMIC RETINOPATHY

[75] Inventor: Jewell L. Osterholm, Radnor, Pa.

[73] Assignee: Thomas Jefferson University, Philadelphia, Pa.

[21] Appl. No.: 901,640

[22] Filed: Aug. 28, 1986

Related U.S. Application Data

[60] Continuation-in-part of Ser. No. 757,015, Jul. 19, 1985, Pat. No. 4,657,532, and Ser. No. 755,427, Jul. 16, 1985, and Ser. No. 582,961, Feb. 23, 1984, Pat. No. 4,686,085, and Ser. No. 428,900, Sep. 30, 1982, abandoned, which is a division of Ser. No. 139,886, Apr. 14, 1980, Pat. No. 4,378,797, said Ser. No. 582,961, is a division of Ser. No. 428,850, Sep. 30, 1982, Pat. No. 4,445,500, which is a division of Ser. No. 354,346, Mar. 3, 1982, Pat. No. 4,445,886, which is a continuation-in-part of Ser. No. 139,886.

[51] Int. Cl.$^4$ .............................. A61M 37/00
[52] U.S. Cl. ............................. 604/24; 604/28; 604/49; 604/51
[58] Field of Search ............ 128/1 R; 604/20, 22–29, 604/51, 49

[56] References Cited

U.S. PATENT DOCUMENTS

| | | | |
|---|---|---|---|
| 3,482,575 | 12/1969 | Claff et al. | 128/214 |
| 3,516,410 | 6/1970 | Hakim | 128/350 |
| 3,583,387 | 6/1971 | Garner | 128/1 |
| 3,626,950 | 12/1971 | Schulte | 128/350 |
| 3,669,094 | 6/1972 | Heyer | 128/2 |
| 3,669,116 | 6/1972 | Heyer | 128/350 |
| 3,690,323 | 9/1972 | Wortman et al. | 128/350 |
| 3,753,865 | 8/1973 | Belzer | 195/127 |
| 3,818,229 | 6/1974 | Long, Jr. | 250/312 |
| 3,823,091 | 7/1974 | Samejima | 252/312 |
| 3,894,541 | 7/1975 | El-Shafei | 128/350 |
| 3,941,119 | 3/1976 | Corrales | 128/2 |

(List continued on next page.)

FOREIGN PATENT DOCUMENTS

| | | |
|---|---|---|
| 4127178 | 11/1978 | Australia . |
| 4295478 | 12/1978 | Australia . |
| 5451380 | 1/1980 | Australia . |
| 6255580 | 9/1980 | Australia . |
| 973094 | 8/1975 | Canada . |
| 1177 | 10/1984 | European Pat. Off. . |
| 2163191 | 7/1982 | Fed. Rep. of Germany . |
| 2118977 | 7/1975 | France . |
| 1381879 | 5/1975 | United Kingdom . |

OTHER PUBLICATIONS

Kohner et al., "The Management of Central Retinal Vein Occlusion", *Ophthalmology*, 90(5) pp. 484–487 (1983).

Hansen et al., "A Randomised Prospective Study on Treatment of Central Retinal Vein Occlusion by Isovolaemic Haemodilution and Photo-Coagulation", *British Jour. of Ophthalmology*, 69:108–116 (1985).

Buzney et al., "Pathogenesis of Diabetic Retinal Angiopathy: Proposed Mechanisms and Current Research", (List continued on next page.)

Primary Examiner—C. Fred Rosenbaum
Assistant Examiner—Mark F. Colosimo
Attorney, Agent, or Firm—Woodcock Washburn Kurtz Mackiewicz & Norris

[57] ABSTRACT

A novel method of treating ischemic retinopathy is disclosed. After diagnosis of ischemic retinopathy, as for example as a result of retinal infarction, the ocular globe is penetrated with two small cannulae. An inflow and outflow perfusion is then established with an oxygenated perfluorochemical emulsion or other physiologically compatible oxygenated liquid. A sufficient perfusion rate is established and maintained to provide the metabolic needs of the retina for the 3 to 5 day period necessary to permit the natural healing process to occur. The method comprises removing at least a portion of vitreous body to create an intraocular perfusion space and establishing a perfusion of physiologically compatible oxygenated fluid through that perfusion space at a rate and for a duration sufficient to permit the natural healing process to occur. Alternatively, a method of diagnosing the condition of retinal tissue suspected of being ischemic is disclosed.

37 Claims, 1 Drawing Sheet

U.S. PATENT DOCUMENTS

| | | | |
|---|---|---|---|
| 3,946,731 | 3/1976 | Lichtenstein | 128/214 |
| 3,962,439 | 6/1976 | Yokoyama et al. | 424/325 |
| 3,975,512 | 8/1976 | Long, Jr. | 424/5 |
| 3,989,843 | 11/1976 | Chabert et al. | 424/325 |
| 4,009,270 | 2/1977 | Gainer, Jr. | 424/325 |
| 4,067,971 | 1/1978 | Francis et al. | |
| 4,070,460 | 1/1978 | Gainer, Jr. | 424/325 |
| 4,073,879 | 2/1978 | Long, Jr. | |
| 4,106,992 | 8/1978 | Vairel et al. | |
| 4,110,474 | 8/1978 | Lagow et al. | 424/350 |
| 4,148,314 | 4/1979 | Yin | 128/214 |
| 4,163,734 | 4/1979 | Sorensen et al. | 252/408 |
| 4,173,224 | 11/1979 | Marx et al. | 128/214 |
| 4,173,654 | 11/1979 | Scherer | 424/350 |
| 4,299,728 | 11/1981 | Cormier et al. | 424/325 |
| 4,340,037 | 7/1982 | Lewicky | |
| 4,393,863 | 7/1983 | Osterholm | 128/1 R |
| 4,402,984 | 9/1983 | Moore | |
| 4,423,077 | 12/1983 | Sloviter | 424/325 |
| 4,443,480 | 4/1984 | Clark, Jr. | 424/352 |
| 4,445,500 | 5/1984 | Osterholm | 128/1 R |
| 4,445,514 | 5/1984 | Osterholm | 128/632 |
| 4,445,886 | 5/1984 | Osterholm | 604/28 |
| 4,445,887 | 5/1984 | Osterholm | 604/28 |
| 4,445,888 | 5/1984 | Osterholm | 604/28 |
| 4,446,154 | 5/1984 | Osterholm | 424/350 |
| 4,446,155 | 5/1984 | Osterholm | 424/355 |
| 4,450,841 | 5/1984 | Osterholm | 128/632 |
| 4,451,251 | 5/1984 | Osterholm | 604/28 |
| 4,496,342 | 1/1985 | Banko | |
| 4,550,022 | 10/1985 | Garabedian et al. | |
| 4,787,797 | 4/1983 | Osterholm | 604/24 |

OTHER PUBLICATIONS

International *Opthalmology Clinics*, 24(4)1–11 (Winter, 1984).

Kanski et al., "Disorders of the Vitreous Retina and Choroid", *Opthalmology I*, Butterworths Int'l. Medical Reviews, London, pp. 115–121 (1983).

Chandler et al., "A Refined Experimental Model for Proliterative Vitreoretinopathy", *Graefe's Arch. Clin. Exp. Ophthalmology*, 224:86–91 (1986).

Lincoff et al., "Use of an Intraocular Gas Tamponode to Find Retinal Breaks", *American Journal of Ophthalmology*, 96:510–546 (1983).

Kreissig et al., "The Treatment of Difficult Retinal Detachments with an Expanding Gas Bubble Without Vitrectomy", *Graefe's Arch. Clin. Exp. Opthalmology*, 224:51–54 (1983).

Haut et al., "Some of the Most Important Properties of Silicone Oil to Explain its Action", *Ophthalmologica Basel*, 191:150–153, (1985).

S. A. Gould et al., *Fed. Proc.* 40:2038 (1981).

Doss, et al., Microvascular Research 13, pp. 253–260 (1977).

Osterholm, J., et al., "Severe Cerebral Ischemia Treatment by Ventriculosubarachnoid Perfusion with an Oxygenated Fluorocarbon Emulsion", *Neurosurgery*, vol. 13, No. 4, pp. 381–387 (1983).

Long et al., "Efficacy and Toxicity Studies with Radiopaque Perfluorocarbon", *Radiology*, 105(2):323–332 (Nov., 1972).

Long et al., "Initial Observations with a New X-Ray Contrast Agent-Radiopaque Perfluorocarbon", *Review of Surgery*, pp. 71–76 (Jan.-Feb., 1972).

*Textbook of Biochemistry with Clinical Correlations*, edited by Thomas M. Devlin, Ph.D., published by John Wiley & Sons New York, 1982, pp. 268–277.

Perfluorochemical Blood Substitutes FC-43 Emulsion Fluosol-DA, 20% and 35% for Preclinical Studies as a Candidate for Erythrocyte Substitution, Naito et al., The Green Cross Corp.

Supplement to Perfluorchemical Blood Substitutes FC-43 Emulsion Fluosol-DA, 20% and 35% as Oxygen Carrying Cooloidal Blood Substitute, Naito et al., The Green Cross Corp.

K. Yokoyama et al., "Development of Fluosol-DA and its Perspective as a Blood Substitute", Symp. 2nd Priestley Conf., Oxygen and Life (1980), published in Supplement to Perfluorochemical Blood Substitutes, The Green Cross Corporation, pp. 28–37.

News Release "Philadelphia Doctor Named Inventor of the Year; Developed Revolutionary System for Treatment of Stroke" *Intellectual Property Owners, Inc.*, Apr. 17, 1985.

Faithfull, N. S. et al., "Whole-body Oxygenation Using Intraperitoneal Perfusion of Fluorocarbons", *British Journal of Anaesthesia*, 56; 867 (1984).

Stedman's Medical Dictionary, Fifth Unabridged Layer's Edition, Anderson Publishing Co., Cincinnati and (List continued on next page.)

OTHER PUBLICATIONS

Jefferson Law Book Company, Washington, D.C. 1982, p. 1181.
Gollon, F. et al., *The Physiologist*, vol. 9, p. 191 (1966).
Sloviter, H. A. et al., *Nature* (London), vol. 216, p. 458 (1967).
Geyer, R. P. *Federation Proceedings*, vol. 29, No. 5, Sep.-Oct., 1970.
Rodnight, R., *Biochemistry Journal*, vol. 57, p. 661.
Clark et al., *Science*, vol. 152, pp. 1755-1756 (1966).
Gollon, F. et al., *Alabama Journal of Medical Science*, vol. 4, p. 336 (1967).
Geyer, R. P., Med u Ernohn, vol. 11, p. 256 (1970).
Krone, W. et al., *Biochemika et Biophysica Acta*, vol. 372, pp. 55-71 (1974).
Rosenblum, W. I., "Fluorocarbon Emulsions and Cerebral Microcirculation," *Federation Proceedings*, vol. 34, No. 6, p. 1493 (May, 1975).
Bose, B. et al., "Focal Cerebral Ischemia: Reduction in Size of Infarcts by Ventriculo-Subarachnoid Perfusion with Fluorocarbon Emulsion", *Brain Research*, 328 (1985), 223-231.
Brochure for the H-1500 Elliptical Oxygenator-Harvey Cardiopulmonary Div. of C. R. Bard, Inc.
Siegel et al., *Basic Neurochemistry*, 2d Little Brown Boston (1978) p. 297.
Kontos, H. A. et al., "Role of Tissue Hypoxemia in Local Regulation of Cerebral Microcirculation," *American Journal of Physiology*, vol. 363, pp. 582-591 (1978).
Hare et al., "Rapid and Sensitive Ion-Exchange Fluorometric Measurement of G-Aminobutyric Acid in Physiological Fluids", *Anal. Biochem.*, vol. 101, pp. 349-355 (1980).
Navari et al., *Res. Exp. Med.*, vol. 170, pp. 169-180 (1977).
Clark et al., *Fed. Proc.*, vol. 34, pp. 1468-1477 (1979).
Osterholm, J. L., *Pathophysiology of Spinal Cord Injury*, C. C. Thomas, Springfield, Illinois (1978).
Pappenheimer, J. R. et al., "Perfusion of the Cerebral Ventricular System in Unanesthized Goats," *Am. J. Physiol.*, vol. 203 No. 5, pp. 763-774 (1962).
Curtis, C., "Blood and Money", *Forbes*, pp. 100-102 (Nov. 9, 1981).
Dirks, et al., "Fluorocarbon Perfusion Medium Applied to the Isolated Rat Brain", *Journal of Pharmacological Methods* 4:95-108 (1980).
Fischer et al., "Reassessment of Cerebral Capillary Changes in Acute Global Ischemia and Their Relationship to the 'No-Reflow Phenomenon'", *Stroke*, vol. 8, pp. 36-39 (1977).
Carey, et al., "The Effect of Severe Hypoglycemia Upon Cerebrospinal Fluid Formation, Ventricular Iodide Clearance, and Brain Electrolytes in Rabbits", *J. Neurosurg.*, Vo. 54, pp. 370-379 (1981).
Chiang, et al. "Cerebral Ischemia: Vascular Changes", *American Journal of Pathology*, Vo. 52, pp. 455-476, (1968).
Clark et al., "Can Fluorocarbon Emulsions be Used as Artificial Blood?" *Triangle*, vol. 11, No. 4, pp. 115-122 (1972).
Britton et al., "Effect of Cerebral Extracellular Fluid Acidity on Total and Regional Cerebral Blood Flow", *Journal of Applied Phys.*, vol. 47, pp. 818-826, Oct.-Dec. (1979).
Brown et al., "Fluorocarbon Sonicated as a Substitute for Erythrocytes in Rat Liver Perfusion", *Surgery*, Vo. 71, No. 3, pp. 388-394 (Mar., 1972).
Callaghan, et al., "CSF Perfusion to Treat Intraventricular Penicillin Toxicity", *Arch. Neurol.*, vol. 38, pp. 390-391 (1981).
Astrup, et al., "The Increase in Extravellular Potassium Concentration in the Ischemic Brain in Relation to the Preischemic Functional Activity and Cerebral Metabolic Rate" *Brain Research*, 199:161-174 (1980).
Ames, et al., "Cerebral Ischemia: II., The No-Reflow Phenomenon" Am. J. Pathol., vol. 52, No. 2, pp. 437-448 (1968).
Berkenbosch et al., "Influence of the CSF Bicarbonate Concentration on the Ventilatory Response to $CO_2$ in Relation to the Location of the Central Chemoreceptors" *Respiration Physiology* 35:215-236 (1978).
Sklar, Ferderick H. et al., "Recirculatory Spinal Subarachnoid Perfusions in Dogs: A Method for Determining CSF Dynamics Under Non-Steady State Conditions," *Neurosurgery*, vol. 1, No. 1, pp. 48-56 (1977).
Sloviter, Henry A. et al., "Erythrocyte Substitute for Perfusion of Brain," *Nature*, vol. 216, pp. 458-460 (Nov. 4, 1967).
Hansebout, Robert R. et al., "Oxygenated Fluorocarbon Perfusion as Treatment of Acute Spinal Cord Compression Injury in Dogs," *J. Neurosurg.*, Vo. 55, pp. 725-732 (1981).
Geyer, et al., "9 Survival of Rats Totally Perfused with a Fluorocarbon-Detergent Preparation", *Organ Perfusion and Preservation*, pp. 85-96 (1968).

OTHER PUBLICATIONS

Glogar et al., "Fluorocarbons Reduce Myocardial Ischemic Damage After Coronary Occlusion", *Science*, vol. 211, pp. 1439–1441 (Mar., 1981).

Gould et al., "How Good are Fluorocarbon Emulsions as $O_2$ Carriers?", Departments of Surgery, Michael Reese Hospital et al., pp. 1–3.

Fischer, E., "Impaired Perfusion Following Cerebrovascular Stasis, *Arch. Neurol.*, Vo. 29, pp. 361–366 (Dec. 1973).

Fritschka, et al., "Total and Regional Cerebral Blood Flow During Perfusion from the Lateral Ventricle to the Cisterna Magna in Conscious Dog: Effect of Hemorrhagic Hypotension and Retransfusion on Cerebral Blood Flow" *Circulatory Shock*, 7:333–342 (1980).

Fritschka, et al., "Increased Free Fatty Acid Turnover in CSF During Hypotension in Dogs", *American J. Physiology*, V. 236, pp. H802–H807, (1979).

Grote, J., "Cerebral Oxygen Supply in Brain Edema and During Ventriculo-Cisternal Perfusion", *Adv. in Exp. Med. Biol.*, vol. 75, pp. 313–324, (1975).

Heisey, et al., "Bulk Flow and Diffusion in the Cerebrospinal Fluid System of the Goat", *American J. of Physic.*, vol. 203, pp. 775–781 (1962).

Hossmann, et al., "Cation Activities in Reversible Ischemia of the Cat Brain", *Stroke*, vol. 8, pp. 77–81 (1977).

Hossmann et al., "Resuscitation in the Monkey Brain After 1 H Complete Ischemia., 1. Physiological and Morphological Observations, *Brain Research*, 81:59–74 (1974).

Hossmann et al., "Reversibility of Ischemic Brain Damage", *Arch. Neurol.*, vol. 29, pp. 375–384 (Dec. 1973).

Javid, et al., "Hypothermic Ventricular Perfusion-- Evaluation of Use in Cerebrovascular Occlusion" *New York State Journal of Medicine*, pp. 248–251 (Jan. 15, 1967).

Kleihues, et al., "Purine Nucletide Metabolism in the Cat Brain After One Hour of Complete Ischemia", *Journal of Neurochemistry*, vol. 23, pp. 417–425 (1974).

Min-Chu Liew et al., "A Technique for Perfusing the Cerebrospinal Fluid Spaces of the Cat from Lateral Ventricle via the Cisterna Magna to the Cortical Subarachnoid Space", *J. Physiol.*, pp. 20P–21P (Dec., 1977).

Martins, et al., "Sources of Error in Measuring Cerebrospinal Fluid Formation by Ventriculocisternal Perfusion", *Journal of Neurosurgery and Phychiatry*, Vo. 40, pp. 645–650, (1977).

Mizoi, et al., "Experimental Study of New Cerebral Protective Substances Functional Recovery of Severe, Incomplete Ischaemic Brain Lesions Pretreated with Mannitol and Fluorocarbon Emulsion *Acta Neurochirurgica* 56, pp. 157–166 (1981).

Peerless, et al., "Protective Effect of Fluosol-DA in Acute Cerebral Ischemia", *Stroke*, vol. 12, No. 5, pp. 558–563, (1981).

Reulen, et al., "Clearance of Edema Fluid into Cerebrospinal Fluid" *J. Neurosurg.* 48: 754–764 (1978).

Schutz, et al., "Brain Mitochondrial Function After Ischemia and Hypoxia", *Arch. Neurol.*, vol. 29, pp. 417–419 (Dec. 1973).

Sokoll, et al., "Dibutyryl Cyclic Adenosine Monophosphate Effects in the Ischemic-Hypoxic Cat", *Stroke*, vol. 8, No. 3, pp. 371–373 (May–Jun., 1977).

J. Suzuki et al., *Current Topics* 9:465–479 (1981).

Tsuyumu, et al., "Dynamics of Formation and Resolution of Vasogenic Brain Oedema I. Measurement of Oedema Clearance into Ventricular CSF", *Acta Neurochirurgica* 57:1–13, (1981).

Tremper, et al., "The Preoperative Treatment of Severely Anemic Patients with a Perfluorochemical Blood Substitute, Fluosol-DA 20%", *Crit. Care Med.* 8 p. 738 (1980).

Weyne et al., "Restoration of $CSF[HCO_3]$ After its Experimental Lowering in Normocapnic Conditions", *J. of Applied Physics*, V. 47, pp. 369–376 (Jul.–Sep. 1979).

Abstract No. [85] Pool Rounds (one page).

Booklet "William Harvey Introduces a New Geometry for Oxygen Performance."

State of the Art Symposium "Artificial Blood", National Institutes of Health, Apr. 5–6, 1974 Federation Proceedings, vol. 34, No. 6, pp. 1428–1517 (1975).

Nordstrom et al., *Acta Physiol. Scand.* (1977).

Siezyo, et al., *Adv. Exp. Med. Biol.* 78; 261–269 (1977).

Clark, et al., *Microvasc. Res.* 8:320–340 (1974).

4,795,423

OXYGENATED PERFLUORINATED PERFUSION OF THE OCULAR GLOBE TO TREAT ISCHEMIC RETINOPATHY

CROSS-REFERENCE TO RELATED APPLICATIONS AND PATENTS

This application is a continuation-in-part of U.S. Ser. No. 428,900, filed Sept. 30, 1982, abandoned, entitled "Stroke Treatment Utilizing Extravascular Circulation Of Oxygenated Synthetic Nutrients To Treat Tissue Hypoxic And Ischemic Disorders" which is a division of Ser. No. 139,886, filed Apr. 14, 1980, now U.S. Pat. No. 4,378,797 and is also a continuation-in-part of U.S. Ser. No. 582,961, filed Feb. 23, 1984, U.S. Pat. No. 4,686,085 of the same title Ser. No. 582,961 is, in turn, a division of Ser. No. 428,850 filed Sept. 30, 1982, now U.S. Pat. No. 4,445,500, which in turn, is a division of Ser. No. 354,346, filed Mar. 3, 1982, now U.S. Pat. No. 4,445,886 and which, in turn, is a continuation-in-part of Ser. No. 139,886, now U.S. Pat. No. 4,378,797, all of which are incorporated herein by reference as if set forth in full.

The present application is also related to the following issued United States patents, all of which are incorporated herein by reference as if set forth in full, and all of which are divisions of one or more of the other of the aforementioned Ser. Nos. 139,886 and 354,346: U.S. Pat. No. 4,445,514; U.S. Pat. No. 4,393,863; U.S. Pat. No. 4,450,841; U.S. Pat. No. 4,445,887; U.S. Pat. No. 4,446,154; U.S. Pat. No. 4,446,155; U.S. Pat. No. 4,451,251; U.S. Pat. No. 4,445,888; U.S. Pat. No. 4,445,500.

The present application is a continuation-in-part of U.S. Ser. No. 755,427, filed July 16, 1985 entitled "Cerebral and Lumbar Perfusion Catheters for Use in Treating Hypoxic and Ischemic Disorders" and of U.S. Ser. No. 757,015, filed July 19, 1985; U.S. Pat. No. 4,657,532 entitled "Intra-Peritoneal Perfusion of Oxygenated Fluorocarbons" each of which applications is also hereby incorporated by reference.

BACKGROUND OF THE INVENTION

The present invention relates to the field of treating ischemic retinopathy, particularly that caused by retinal infarction.

Ischemic retinopathy is a major cause of blindness. Retinal ischemia may result from a number of different causes and may be associated with other diseases and conditions, such diabetes, atherosclerosis, etc. For example, retinal ischemia caused by central retinal vein occlusion (CRVO). CRVO may result from a number of different underlying conditions.

A number of treatments have been suggested for retinal ischemia. For example, to manage outflow obstruction, it has been suggested to administer fibrinolytic agents and anticoagulants, to conduct hemodilution and plasma exchange, to administer steroids, or to conduct photocoagulation. See Kohner et al, "The Management of Central Retinal Vein Occlusion", *Ophthalmology*, 90(5): 484–487 (1983). Unfortunately, the aforementioned treatments have not been found very effective. See also Hansen et al, "A Randomised Prospective Study on Treatment of Central Retinal Vein Occlusion by Isovolaemic Haemodilution and Photocoagulation", *British Journal of Ophthalmology*, 69:108–116 (1985).

The prognosis for diabetic retinal angiopathy is not very encouraging. See Buzney et al, "Pathogenesis of Diabetic Retinal Angiopathy: Proposed Mechanisms and Current Research", *International Ophthalmology Clinics*, 24(4):1–11 (Winter, 1984). Buzney et al recognize that a need exists to develop new methods of treating diabetic retinal angiopathy, suggesting that research efforts will "someday produce chemotherapeutic methods that will exceed the scope of laser or vitreoretinal surgery". Buzney et al hypothesize that the systemic use of such chemotherapeutic agents may be supplemented "by injection into the vitreous chamber or even the use of a vitreous substitute that fully tamponades the retina, inactivating or selecting inhibiting the diffusion of vasoactive substances". See Buzney et al at page 9.

While some of the aetiologies of retinal vein occlusion are well understood, others are only partially so, and in still others the cause remains obscure. Systemic hypertension is recognized as a cause of certain occlusions, as is the inflammation of the vein wall (periphlebitis) and glaucoma. As discussed in Kanski et al, "Disorders of the Vitreous, Retina and Choroid", *Ophthalmology I*, pp. 115–121, Butterworths International Medical Reviews, London, (1983), the conventional treatments for retinal vein occlusion are systemic drug administration and photocoagulation, neither of which are consistently effective.

Although generally unrelated to the management of central retinal vein occlusion or other retinal ischemias, it is known to introduce a variety of liquids or gases into the ocular globe for a variety of reasons. For example, in Chandler et al, "A Refined Experimental Model for Proliferative Vitreoretinopathy", *Graefe's Arch Clin. Exp. Ophthalmol*, 224:86–91 (1986), experiments are described wherein the intact vitreous region is injected with large numbers of tissue cultured fibroblasts. However, such injections were not found to induce the disease as it is found in humans. In Lincoff et al, "Use of an Intraocular Gas Tamponade to Find Retinal Breaks", *American Journal of Ophthalmology*, 96:510–516 (1983), the subretinal fluid was drained and the volume replaced by a perfluorocarbon gas calculated to fill the eye below the probable level of the retinal break. The bubble closed the break and maintained reattachment until the gas was absorbed.

In Kreissig et al, "The Treatment of Difficult Retinal Detachments with an Expanding Gas Bubble Without Vitrectomy", *Graefe's Arch. Clin. Exp Ophthalmology* 224:51–54 (1986). A prospective study is reported using perfluorocarbon gases ($CF_4$, $C_2F_6$, $C_3F_8$) without prior mechanical vitrectomy.

In Haut et al, "Some of the Most Important Properties of Silicone Oil to Explain its Action", *Ophthalmologica*, Basel 191:150–153 (1985), the action of silicone oil used to close tears and reattach the retina is disclosed. The action of such silicone oil is described as being a result of its density and surface tension causing the bubble to press upon the upper part of the eye, i.e., most of the time at twelve o'clock so there is constant support upwards which closes the tears and reattaches the retina.

Notwithstanding what is known in this area, there is a long felt need for effect methods to treat ischemic retinopathy.

SUMMARY OF THE INVENTION

The present invention provides a novel method for treating ischemic retinopathy and/or retinal ischemia.

The method comprises the steps of removing all or at least a portion of the vitreous body to create an intraocular perfusion space, and establishing a perfusion of physiologically compatible oxygenated nutrient liquid through said perfusion space to support the metabolic needs of the retina until natural healing occurs.

Preferably, the step of removing a portion of the vitreous body comprises creating an incision at the limbus of the eye adjacent to the irido-corneal angle, and then using an ultrasonic desecrator. The amount of vitreous body which is actually removed will depend to some extent upon the effect of such removal upon the condition of the underlying retina, however, in any event, a sufficient portion, if not all, of the vitreous body will be removed such that the subsequent establishment of a perfusion through the chamber thus created will be suffiient to expose the ischemic region of the retina to effective amounts of perfused oxygenated liquid.

A circulatory perfusion of physiologically compatible oxygenated nutrient liquid is established by inserting input and output cannulae through the irido-corneal region of the eye, suturing them in place. Using an oxygenated perfluorocarbon emulsion of the type disclosed in the aforementioned Osterholm U.S. patents (which have been incorporated by reference herein), a perfusion rate of between about 0.25 to 10 mls per minute is established at a perfusion pressure which is no greater than the normal vitreous pressure of the eye. The subject perfusion is established through said cannulae, which are preferably 18 to 25 gauge cannulae, the inner termini of which are suitably positioned within the intraocular perfusion space created by the removal of the vitreous body to thereby cause oxygenated perfluorocarbon emulsion to wash across the ischemic region to be treated. The oxygenated liquid should then be perfused for about 3–5 days at a rate which is sufficient to support the metabolic needs of the retina until normal healing occurs.

In order to determine the progress of such healing and/or the sufficiency of the subject treatment to maintain the metabolic needs of the retina, perfusion with oxygenated fluorocarbon emulsion, which is a milky white substance, should be periodically interrupted in favor of a clear physiologic saline solution which will allow visual observation of the retina and, depending upon the patient's condition, vision.

At the conclusion of treatment, any residual perfluorocarbon emulsion is washed from the intraocular perfusion space and is replaced with a conventional synthetic vitreous solution or gel to replace the vitreous body, the cannulae are removed, and the ocular globe is resealed. Since a relatively small surface area of tissue is exposed to the perfluorocarbon, and since the perfluorocarbon emulsion is formulated to be physiologically compatible, systemic side effects should not be observed.

The present invention also provides a novel method for diagnosing the condition of retinal tissue suspected of being ischemic. This method comprises the steps of removing at least a portion of vitreous body to create an intraocular perfusion space adjacent to the retina; establishing a circulation of a physiologically compatible liquid of known composition through said perfusion space by injecting said liquid into and withdrawing said liquid from said perfusion space; and analyzing said liquid withdrawn from said intraocular perfusion space to determine at least one characteristic of said withdrawn fluid which differs from said fluid as injected and which is representative of the condition of said retinal tissue. In accordance with this preferred diagnostic method, the withdrawn fluid is analyzed for any one of a variety of compositional characteristics, such as oxygen content, lactate acid concentration, carbon dioxide concentration, ammonia concentration, pH, etc. As a result, the attending physician may monitor the progress of the treatment for retinal ischemia and/or of underlying healing processes using objective physical or chemical means.

Accordingly, the present invention provides a novel method for treating retinal ischemia to prevent blindness. This and other objects of the present invention will become apparent from the following, more detailed description.

DETAILED DESCRIPTION OF THE PREFERRED EMBODIMENTS

Figure 1:
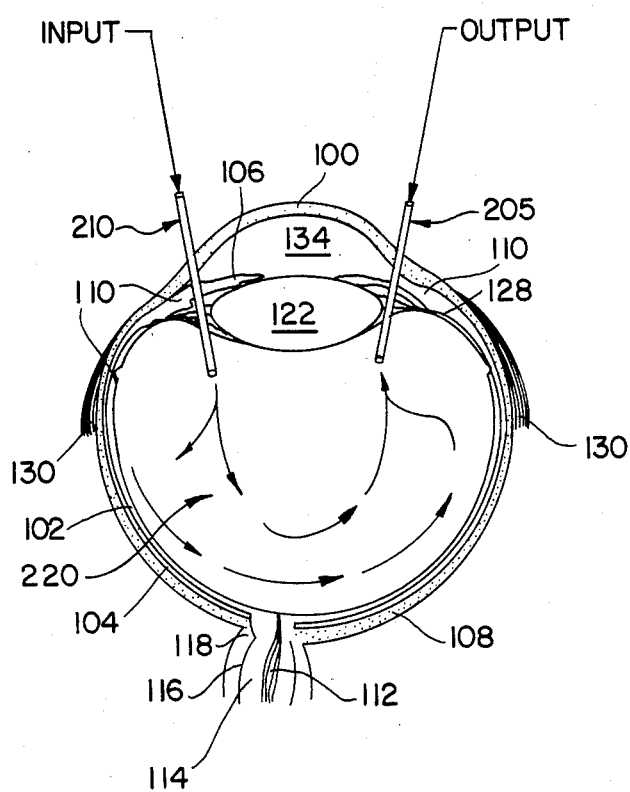
FIG. 1 is a diagrammatic horizontal section of the eyeball illustrating the intraocular perfusion established by the method of the present invention.

The present invention provides a novel method of treating retinal ischemia. As seen in FIG. 1, the retina 102 is the internal coat of the eye. The retina 102 is disposed over the middle or vascular coat of the eye, which coat comprises the choroid 104, ciliary body 110 and iris 106. The eyeball further comprises an external or fibrous coat comprising the transparent cornea 100 and sclera 108. Behind the cornea is aqueous humor 134 which fills two chambers, an anterior one in front of the iris and a posterior one behind the iris. The lens 122 is located behind the aqueous humor and is suspended by suspensory ligaments which extend generally from the sides of the lens towards the ciliary process 128. The vitreous body, which is a jelly-like substance disposed within the vitreous membrane, is normally disposed behind the lens occupying the vitreous chamber. In the eye illustrated in FIG. 1, however, the vitreous body has been removed to create in the vitreous chamber an intraocular perfusion space designated generally 220. Accordingly, the retina 102, which comprises an outer layer pigmented cells and an inner layer of optic cells (which layers are not shown in the drawing) are directly exposed to the intraocular perfusion space. The central artery and vein of the retina 112 supply the retina in the region of the optic nerve, which is surrounded by an internal sheath 114 and an intervaginal subarachnoid space 116. The nerve further comprises an external neural sheath 118. External muscles 130 attached to the sclera assist in rotating the eyeball.

In accordance with the preferred embodiment of the present invention, the entirety of the vitreous body is removed to create an intraocular perfusion space 220, adjacent to the portion of the retina to be treated. The vitreous body may be removed by creating an incision at the limbus of the eye adjacent to the irido-corneal angle, and using an ultrasonic desecrator with suction (such as the CUSA desecrator to remove the vitreous body. Following removal of the vitreous body, small catheters or cannulae 205 and 210 are inserted through the irido-corneal angle into the intraocular perfusion space 220 thus created. Those of ordinary skill in ocular surgery will recognize that the placement of these cannulae may differ somewhat from that shown in FIG. 1. Each of catheters 205 and 210 are sutured water-tight in place. Once in place, an intraocular circulation should be established using a physiologic oxygenated liquid which is capable of providing for the metabolic needs of the affected retina.

The preferred oxygenated liquid of the present invention is that which is disclosed in the aforementioned Osterholm patents which have been incorporated by reference herein. See for example, the disclosure of U.S. Pat. No. 4,450,841 at columns 15-20. The preferred physiologic oxygenated liquid of the present invention is a nutrient emulsion comprised of carefully formulated components including electrolytes (sodium, potassium, calcium, magnesium and chloride) and a non-aqueous oxygen transfer component (such as a perfluorobutyltetrahydrofuran which has been sold by the 3-M Corporation under the trademark "FC-80" or "RIEMAR's RM-101". The preferred non-aqueous oxygen transfer component of the preferred nutrient liquid should exhibit, when charged oxygen, vapor pressures in the range above about 400, and preferably above 600 Torr. Such oxygen transfer components similarly should not exhibit high vapor pressures which would boil at body temperatures, nor have viscosities which are difficult if not impossible to emulsify. It is presently anticipated that other fluorocarbon compounds may be found suitable for use in performing the methods of the present invention, including such fluorocarbons as PFOB, those which can be emulsified at very small (less than 2mu particle sizes) to be clear, and/or those containing 2 or more aromatic rings. While emulsions prepared from fluorocarbons such as perfluorobutyltetrahydrofuran are milky white in color, most desired would be to utilize a fluorocarbon emulsion which is clear, and which therefore would not interfere with vision or visual retinal observation during treatment. In addition to the aforementioned components, the subject emulsions should have an emulsification component, which may be any one of a number of known fluorocarbon emulsifiers, of which block polymer polyols, such as a pluronic, is representative. The osmolarity of the subject emulsion should be controlled within a range of about 290-330 mOsM, with the slightly higher range of 220-230 being preferred to lessen swelling and reduce pressure within the eye. In addition to the aforementioned components, the subject emulsion preferably comprises glucose, amino acids, steroids, antibiotics, etc., as disclosed more fully in the aforementioned U.S. patents which have been incorporated herein by reference.

Once the vitreous body has been removed and the cannulae inserted, an intraocular perfusion may be established. During the intraocular perfusion, it may be desired to ensure the stability of the subject catheters by using an external appliance (Dutchman) to fix their positions with respect to the eye. Although two catheters are presently illustrated, it is also within the scope of the present invention to utilize a single double lumen catheter which has separate input and output locations to similarly create the desired intraocular perfusion across the retinal surface to be treated.

The oxygenated nutrient emulsion may be delivered at room temperature, that is at about 24° C., however higher or lower temperatures may be used to deliver the oxygenated nutrient emulsions as medical conditions warrant.

In accordance with the preferred method of the present invention, sufficient nutrient emulsion should be supplied to counteract oxygen and other metabolite deprivation of the effected retinal tissue. It is currently anticipated that perfusion rates as much as 10 mls/min may be established at normal vitreous pressures, however, flows of as little as 2.5 ml/min may be sufficient to treat certain affected regions of ischemic retinal tissue.

It is preferred to establish the circulation of physiologically compatible oxygenated liquid as quickly as possible upon the diagnosis of retinal infarction. The circulation may be maintained awaiting normal healing, or surgical procedures may be used to reestablish blood supply to the effected portion of the retina. In either event, once the retina is able to sustain itself without perfusion, the perfused liquid will be allowed to remain in the globe if transparent, or preferably may be replaced by physiologically compatible synthetic vitreous humor.

Accordingly, the method of the present invention takes advantage of the fact that the retina is of the same neural origin as the brain, and follow the same response to ischemia as does the brain. In these terms, while the retina has relatively poor tolerance to ischemia and undergoes infarction resulting in partial or complete visual loss, it is also susceptible to artificial maintenance through the use of physiologic oxygenated fluorocarbon emulsions which have been found suitable for maintaining the viability of neural tissue in other locations, such as the brain and spinal cord.

Anatomically, the optic globe has features analogous to the brain. The retina is adjacent to a body of fluid (vitreous humor), similar to the brain's relationship to the cerebrospinal fluid. The vitreous humor can be removed without lasting harm to vision as long as the shape of the globe is not permitted to undergo major distortion. Accordingly, the vitreous humor can be aspirated and replaced with a physiologic salt solution without perturbing visual function. This group of factors, i.e., anatomic proximity, replaceable fluid, and similarity of the retina to the brain all favor this approach to resuscitating retinal tissue which otherwise will be irretrievably lost.

It is also within the scope of the present invention to diagnosis the condition of the retina by analyzing the physical and chemical characteristics of the perfusate after it is withdrawn from output catheter 205. The fluid which is withdrawn from the intraocular perfusion space will not be of identical composition to the oxygenated nutrient emulsion which is injected through input catheter 210. By taking advantages of differences in the composition which are detected in the withdrawn fluid, which may be considered to have become a diagnostic fluid, the attending physician may easily monitor the physiologic condition of the neurologic retinal tissue which is being treated. This diagnostic fluid may also be monitored to assure that treatment is proceeding according to plan. Accordingly, fluid which is drawn from the intraocular perfusion space may be analyzed for characteristics including potassium and sodium ion concentration, lactic acid concentration, gamma aminobutyric acid (GABA) and other amino acid concentrations, oxygen concentration, carbon dioxide concentration, enzyme concentration, microorganism (bacterial) content, ammonia concentration, myelin fragments, cellular materials including organelles, proteins, fats, RNA, DNA, metabolites, metabolic products, pH and/or neurotransmitter content. This diagnostic method takes advantage of the fact that ischemic neurologic tissue produces higher concentrations of such materials as GABA, lactate ion, enzymes, and/or LDH (lactate dehydrogenase), ammonia, and other constituents which have been determined by analyzing cerebrospinal fluid of patients subjected by disease to anoxic conditions or neural tissue. In accordance with the method of the present invention, a continuous monitoring of the state of the neurologic tissue is possible since the circulation of oxygen in nutrient emulsion will produce a continuous flushing of the affected retinal tissue, and thus will result in diagnostic fluid component variations which are rapidly reflective of the physiologic state of the tissue being treated.

Accordingly, novel diagnostic and therapeutic methods are provided by the present invention for treating ischemic retinopathy, particular retinal infarctions, which otherwise may result in blindness.

Those of ordinary skill in this art will recognize that various changes in the materials and methods described herein can be made without departing from the scope of the present invention which is defined more particularly in the claims appended hereto.

What is claimed:

1. A method of treating retinal ischemia, comprising the steps of:
    a. removing at least a portion of the vitreous body to create an intra-ocular perfusion space; and
    b. establising a circulation of a physiologically compatible oxygenated liquid through said perfusion space by injecting said liquid into and withdrawing said liquid from said space.

2. The method of claim I wherein said removing step comprises creating an incision at the limbus of the eye adjacent to the irido-corneal angle.

3. The method of claim 2 wherein said removing step comprises using an ultrasonic desecrator to remove a portion of the vitreous body.

4. The method of claim 1 wherein step (b) further comprises inserting input and output cannulae through the irido-corneal region of the eye.

5. The method of claim 1 wherein said circulation is established at a rate of between about 0.25 to 10 ml/min.

6. The method of claim 5 wherein said circulation is conducted at a pressure of no greater than the normal vitreous pressure of said eye.

7. The method of claim I wherein step (b) comprises inserting an 18 to 25 gauge cannulae into said intraocular perfusion space.

8. The method of claim 1 wherein said oxygenated liquid is circulated for a duration and at a rate sufficient to support the aerobic metabolism of the retina until healing occurs.

9. The method of claim 1 further comprising the step of periodically circulating through said perfusion space a transparent solution.

10. The method of claim I wherein said vitreous body is removed at least in the region adjacent to ischemic retinal tissue to be treated.

11. The method of claim 10 wherein said vitreous body is substantially completely removed.

12. A method of diagnosing the condition of retinal tissue suspected of being ischemic, comprising the steps of:
    a. removing at least a portion of vitreous body to create an intracellular perfusion space adjacent to said retina;
    b. establishing a circulation of a physiologically compatible liquid of known composition through said space by injecting said liquid into contact with said tissue and withdrawing said liquid from said space; and
    c. analyzing said liquid withdrawn from said intraocular perfusion space to determine at least one characteristic of said withdrawn liquid which differs from said liquid as injected.

13. The method of claim 12 wherein said method further comprises comparing constituents of said liquid for at least a selected difference in the composition of said injected and withdrawn liquids.

14. The invention of claim 13 wherein said selected difference is a difference in oxygen content.

15. The invention of claim 13 wherein said selected difference is a difference in lactic acid concentration.

16. The invention of claim 13 wherein said selected difference is a difference in carbon dioxide concentration.

17. The invention of claim 13 wherein said selected difference is a difference in ammonia concentration.

18. The invention of claim 13 wherein said selected difference is a difference in enzyme content.

19. The invention of claim 13 wherein said difference is a difference in pH.

20. The invention of claim 13 wherein said difference is a difference in GABA.

21. The invention of claim 13 wherein said difference is a difference in microorganism contents.

22. The invention of claim 21 wherein said microorganism content is a bacterial content.

23. The invention of claim 13 wherein said difference is a difference in ion concentration.

24. The invention of claim 23 wherein said ion concentration difference is a sodium ion concentration difference.

25. The invention of claim 23 wherein said difference is the difference in concentration of potassium ions.

26. The invention of claim 13 wherein said difference is a difference in amino acid concentration.

27. The invention of claim 13 wherein said difference is a difference in concentration of myelin fragments.

28. The invention of claim 13 wherein said difference is a difference in identifiable cellular materials.

29. The invention of claim 13 wherein said difference is a difference in concentration of identifiable cellular organelles.

30. The invention of claim 13 wherein said difference is a difference in protein.

31. The invention of claim 13 wherein said difference is a difference in fats.

32. The invention of claim 13 wherein said difference is a difference in fat content.

33. The invention of claim 13 wherein said difference is a difference in RNA content.

34. The invention of claim 13 wherein said difference is a difference in DNA content.

35. The invention of claim 13 wherein said difference is a difference in cellular metabolic products.

36. The invention of claim 13 wherein said difference is a difference in metabolite content.

37. The invention of claim 13 wherein said difference is a difference in neurotransmitter content.

* * * * *